United States Patent
Zecchino

(10) Patent No.: US 9,474,708 B2
(45) Date of Patent: Oct. 25, 2016

(54) TRITIGHTENING SKIN CARE FORMULATION

(71) Applicant: Julius Zecchino, New York, NY (US)

(72) Inventor: Julius Zecchino, New York, NY (US)

( * ) Notice: Subject to any disclaimer, the term of this patent is extended or adjusted under 35 U.S.C. 154(b) by 23 days.

(21) Appl. No.: 13/998,617

(22) Filed: Nov. 18, 2013

(65) Prior Publication Data

US 2016/0008259 A1  Jan. 14, 2016

(51) Int. Cl.
| | |
|---|---|
| *A61K 8/365* | (2006.01) |
| *A61Q 19/08* | (2006.01) |
| *A61K 8/73* | (2006.01) |
| *A61K 8/88* | (2006.01) |
| *A61K 8/60* | (2006.01) |
| *A61K 8/368* | (2006.01) |
| *A61Q 19/00* | (2006.01) |
| *A61K 8/85* | (2006.01) |
| *A61Q 1/02* | (2006.01) |

(52) U.S. Cl.
CPC ................. *A61K 8/88* (2013.01); *A61K 8/365* (2013.01); *A61K 8/368* (2013.01); *A61K 8/606* (2013.01); *A61K 8/735* (2013.01); *A61K 8/85* (2013.01); *A61Q 19/00* (2013.01); *A61Q 1/02* (2013.01); *A61Q 19/08* (2013.01)

(58) Field of Classification Search
CPC ...... A61K 8/362; A61K 8/365; A61Q 19/08; A61Q 19/007
See application file for complete search history.

(56) References Cited

U.S. PATENT DOCUMENTS

| | | | | |
|---|---|---|---|---|
| 5,677,339 | A * | 10/1997 | Yu | A61K 8/26 514/557 |
| 2004/0156802 | A1* | 8/2004 | Iwasaki | A61K 8/0212 424/70.1 |
| 2006/0153785 | A1* | 7/2006 | Ho | A61K 8/042 424/61 |
| 2007/0053854 | A1* | 3/2007 | Pantini | A61K 8/70 424/59 |
| 2008/0226756 | A1* | 9/2008 | Willemin | A61K 8/602 424/732 |

\* cited by examiner

*Primary Examiner* — Gina Justice
(74) *Attorney, Agent, or Firm* — Dan DeLa Rosa

(57) ABSTRACT

The present invention provides for a formulation comprising: at least one hydrophilic polymer, at least one desquamatory agent and alpha hydroxyl acid.

10 Claims, No Drawings

TRITIGHTENING SKIN CARE FORMULATION

BACKGROUND OF INVENTION

1. Field of Invention

The present invention relates a skin care formulation and related method of manufacture. In particular, the present invention provides for a skin care formulation with a tri-tightening complex including a hydrophilic polymer, a desquamatory agent and an alpha hydroxyl acid.

2. Description of Related Art

There are numerous prior art patents that disclose skin tightening properties. The present invention provides for a skin care formulation with a tri-tightening complex.

SUMMARY OF INVENTION

In one embodiment, the present invention provides for a formulation comprising: at least one hydrophilic polymer, at least one desquamatory agent and alpha hydroxyl acid.

In another embodiment, the hydrophilic polymer is selected from a group consisting essentially of polyglutamic acid (PGA), crosslinked polyglutamic acid, crosslinked hyaluronic acid, cross-linked poly lactic acid, and combination and mixtures thereof.

In yet another embodiment, the desquamatory agent is selected from a group consisting essentially of N-acetyl glucosamine (NAG), glucosamine, glucosamine hydrochloride and combination and mixtures thereof.

In still another embodiment, the alpha hydroxyl acid is mandelic acid.

In still yet another embodiment, the formulation further comprises water. In a further embodiment, the formulation can be used as a product selected from a group consisting of skin care products, cosmetics, cosmeceuticals, pharmaceuticals and nutriceuticals. In another further embodiment, the formulation can be combined with other components and ingredients to form a product selected from a group consisting of skin care products, cosmetics, cosmeceuticals, pharmaceuticals and nutriceuticals.

In yet a further embodiment, the formulation further comprises an activator selected from a group consisting essentially of Water, Glycerin, Glycols, Polyols, Polyglutamic Acid, Hyaluronic Acid, and combination and mixtures thereof. In still a further embodiment, the formulation further comprises preservatives, flavoring and coloring agents.

In still yet a further embodiment, the hydrophilic polymer has increased molecular weight. In yet another further embodiment, the hydrophilic polymer is cross-linked. In still another further embodiment, the alpha hydroxyl acid has increased molecular weight.

In still yet another embodiment, the present invention relates to a composition comprising polyglutamic acid, mandelic acid and N-acetyl glucosamine. In another embodiment, the polyglutamic acid has increased molecular weight. In yet another embodiment, the polyglutamic acid is cross-linked. In still another embodiment, the alpha hydroxyl acid has increased molecular weight.

In still yet another embodiment, the composition further comprises water. In a further embodiment, the composition can be used as a product selected from a group consisting of skin care products, cosmetics, cosmeceuticals, pharmaceuticals and nutriceuticals. In another further embodiment, the composition can be combined with other components and ingredients to form a product selected from a group consisting of skin care products, cosmetics, cosmeceuticals, pharmaceuticals and nutriceuticals.

In yet a further embodiment, the composition further comprises an activator selected from a group consisting essentially of Water, Glycerin, Glycols, Polyols, Polyglutamic Acid, Hyaluronic Acid, and combination and mixtures thereof.

In still a further embodiment, the composition further comprises preservatives, flavoring and coloring agents.

In still yet a further embodiment, the formulation manufactured by a process comprising: providing at least one hydrophilic polymer, at least one desquamatory agent and alpha hydroxyl acid; increasing the molecular weight of the hydrophilic polymer; crosslinking the hydrophilic polymer; increasing the molecular weight of the alpha hydroxyl acid; and admixing the hydrophilic polymer, the desquamatory agent and the alpha hydroxyl acid to make a formulation.

In another embodiment, the process further comprises admixing water.

In another further embodiment, the hydrophilic polymer is from about 0.05% to about 0.3%, said desquamatory agent is from about 0.05% to about 40% and said alpha hydroxyl acid is from about 0.05% to about 30% of the formulation.

In yet another further embodiment, the formulation can be used as a product selected from a group consisting of skin care products, cosmetics, cosmeceuticals, pharmaceuticals and nutriceuticals.

In still another embodiment, the formulation is designed to be combined with other components and ingredients to form a product selected from a group consisting of skin care products, cosmetics, cosmeceuticals, pharmaceuticals and nutriceuticals.

In still yet another embodiment, the process further comprises admixing at least one activator selected from a group consisting essentially of Water, Glycerin, Glycols, Polyols, Polyglutamic Acid, Hyaluronic Acid, and combination and mixtures thereof.

In a further embodiment, the process further comprises admixing preservatives, flavoring and coloring agents.

DETAILED DESCRIPTION OF THE INVENTION

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

In one embodiment, the present invention uses Polyglutamic acid (PGA) as the hydrophilic polymer. PGA has been used as a long term skin hydrating, plumping material. The material helps bind water to the skin, plumping the stratum corneum, adding to skin firming and reducing lines and wrinkles.

These polymers have usually been in the one to two thousand Dalton ranges with the maximum molecular weight of 10,000 Daltons. Recently, breakthroughs in biotechnology have produced polymers in the 2 to 3 million Dalton range. These high molecular weight PGAs retain much more water on the skin than the lower molecular weight ones. They actually hold more moisture than the Industry standard, hyaluronic acids, that have molecular weights in the 2 million Dalton range. In addition, a special grade of PGA was employed in this invention. A PGA with a molecular weight of about 2 million Daltons, that is additionally cross-linked. This cross-linking helps render the polymer to be more long lasting on the skin surface. It makes it less sensitive to degradation by skin enzymes and other agents. The high molecular weight cross-linked PGA provides a longer lasting firming and plumping effect than that of other PGA's and hyaluronic acid.

In yet another embodiment, the present invention may use Mandelic Acid which is a large molecular weight alpha hydroxy acid. Mandelic acid contains an aromatic ring that makes it slow to penetrate the upper layers of the stratum corneum. This helps to have a much more prolonged effect on the skin than other alpha hydroxy acids like glycolic or lactic acids. The skin resurfacing action of mandelic acid has numerous benefits: firstly, it has been shown to clip off dead surface skin cells, and secondly, makes the action of PGA better by giving it a smooth undisturbed surface to bind moisture to. Thusly, mandelic acid contributes to the skin firming and smoothing benefits of the skin care formulations of the present invention.

In still another embodiment, the desquamatory agent may be N-acetyl glucosamine (NAG). NAG has shown to give excellent results in skin smoothness, firming and reducing lines and wrinkles. It acts as a natural skin desquamatory, gently clipping off skin surface cells that are remaining on the surface too long. There also appears to be a retinoid-like effect of increasing collagen synthesis and improving dermal thickening. NAG assist in making the skin denser and less lined and wrinkled. The addition of NAG to mandelic acid and cross-linked PGA, appears to yield an optimum amount of skin firming that is recognizable on test subjects in two to four weeks.

The following examples are set forth below:

Example 1

Tri-Tightening Complex Formulation A

Phase A is weighed in a kettle equipped with high speed agitation. Phase B is then added to Phase A and mixed until homogenous. The ingredients and percentage of each ingredient in the composition is set forth in Table 1 below:

TABLE 1

| Phase: | Ingredients: | Percentage: |
|---|---|---|
| A | Water | 58.100 |
|  | Mega Moist | 0.500 |
|  | N-Acetyl D-Glucosamine | 4.000 |
|  | Mandelic Acid | 0.500 |
|  | Ritaloe 1 X | 1.000 |
|  | Citric Acid | 0.100 |
|  | Sodium Citrate | 0.300 |
| B | Alcohol | 35.000 |
|  | Phenoyxethanol | 0.500 |
| Total Percentage: |  | 100.000 |

Example 2

Tri-Tightening Complex Formulation B

Phase A is weighed in a kettle equipped with high speed agitation. The ingredients and percentage of each ingredient in the composition is set forth in Table 2 below:

TABLE 2

| Phase: | Ingredients: | Percentage: |
|---|---|---|
| A | Water | 93.100 |
|  | Mega Moist | 0.500 |
|  | N-Acetyl D-Glucosamine | 4.000 |
|  | Mandelic Acid | 0.500 |
|  | Ritaloe 1 X | 1.000 |
|  | Citric Acid | 0.100 |
|  | Sodium Citrate | 0.300 |
|  | Phenoyxethanol | 0.500 |
| Total Percentage: |  | 100.00 |

The present invention is not limited to the above Examples and Tables. Numerous modifications and variations of the present invention are possible in light of the above teachings. It is therefore to be understood that within the scope of the attendant claims attached hereto, this invention may be practiced other than as specifically disclosed herein.

What is claimed is:

1. A formulation consisting of: at least one hydrophilic polymer, at least one desquamatory agent, water, at least one additive, preservatives, flavoring and coloring agents and alpha hydroxyl acid, said hydrophilic polymer is selected from a group consisting of polyglutamic acid (PGA), cross-linked polyglutamic acid, crosslinked hyaluronic acid, cross-linked poly lactic acid, and combination and mixtures thereof, said desquamatory agent is selected from a group consisting of N-acetyl glucosamine (NAG), glucosamine, glucosamine hydrochloride and combination and mixtures thereof, said additive is selected from a group consisting of water, glycerin, glycols, polyols, polyglutamic acid, hyaluronic acid, and combinations and mixtures thereof, and said alpha hydroxyl acid is mandelic acid.

2. The formulation of claim 1 wherein said formulation can be used as a product selected from a group consisting of skin care products, cosmetics, cosmeceuticals, pharmaceuticals and nutriceuticals.

3. The formulation of claim 1 wherein said hydrophilic polymer has a molecular weight from about 10,000 Daltons to about 3,000,000 Daltons.

4. The formulation of claim 1 wherein said hydrophilic polymer is cross-linked.

5. A composition consisting of: polyglutamic acid, mandelic acid, N-acetyl glucosamine, water, at least one activator, preservatives, flavoring and coloring agents and combinations and mixtures thereof.

6. The composition of claim 5 wherein said polyglutamic acid has a molecular weight from about 10,000 Daltons to about 3,000,000 Daltons.

7. The composition of claim 5 wherein said polyglutamic acid is cross-linked.

8. The composition of claim 5 wherein said composition can be used as a product selected from a group consisting of skin care products, cosmetics, cosmeceuticals, pharmaceuticals and nutriceuticals.

9. A composition consisting of: at least one hydrophilic polymer, at least one desquamatory agent, water, at least one additive, and alpha hydroxyl acid, said hydrophilic polymer is selected from a group consisting of polyglutamic acid (PGA), crosslinked polyglutamic acid, crosslinked hyaluronic acid, cross-linked poly lactic acid, and combination and mixtures thereof, said desquamatory agent is selected from a group consisting of N-acetyl glucosamine (NAG), glucosamine, glucosamine hydrochloride and combination and mixtures thereof, said additive is selected from a group consisting of water, glycerin, glycols, polyols, polyglutamic acid, hyaluronic acid, and combinations and mixtures thereof, and said alpha hydroxyl acid is mandelic acid.

10. The composition of claim 9 wherein said composition can be used as a product selected from a group consisting of skin care products, cosmetics, cosmeceuticals, pharmaceuticals and nutriceuticals.

* * * * *